United States Patent
Graveley et al.

(10) Patent No.: US 11,849,918 B2
(45) Date of Patent: Dec. 26, 2023

(54) COUPLING OF MEDICAL DEVICE COMPONENTS

(71) Applicant: Boston Scientific Scimed Inc., Maple Grove, MN (US)

(72) Inventors: Andrew Graveley, Indianapolis, IN (US); Adam Larouche, Indianapolis, IN (US); Daniel Eads, Solsberry, IN (US); Steve Pickett, Spencer, IN (US); Caleb McDaniel, Bloomington, IN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 131 days.

(21) Appl. No.: 17/166,780

(22) Filed: Feb. 3, 2021

(65) Prior Publication Data

US 2021/0235970 A1   Aug. 5, 2021

Related U.S. Application Data

(60) Provisional application No. 62/969,837, filed on Feb. 4, 2020.

(51) Int. Cl.
*A61B 1/00* (2006.01)
*A61B 1/018* (2006.01)
(Continued)

(52) U.S. Cl.
CPC ........ *A61B 1/00101* (2013.01); *A61B 1/0011* (2013.01); *A61B 1/0014* (2013.01);
(Continued)

(58) Field of Classification Search
CPC . A61B 1/00101; A61B 1/00098; A61B 1/018; A61B 1/00137
See application file for complete search history.

(56) References Cited

U.S. PATENT DOCUMENTS 4,004,443 A * 1/1977 Gavinet ................. B21C 26/00
                                                            277/467
4,350,150 A * 9/1982 Kubota .............. G02B 23/2469
                                                            600/176
(Continued)

FOREIGN PATENT DOCUMENTS

| DE | 102017100867 | 6/2018 |
|---|---|---|
| EP | 3351217 | 7/2018 |
| WO | WO 0007502 | 2/2000 |

OTHER PUBLICATIONS

International Search Report and Written Opinion issued in International Application No. PCT/US2021/016349, dated Jun. 7, 2021 (10 pages).

*Primary Examiner* — John P Leubecker
*Assistant Examiner* — Jae Woo
(74) *Attorney, Agent, or Firm* — Bookoff McAndrews, PLLC (57) ABSTRACT

A distal end portion of a medical device may comprise: a first portion having a groove around a perimeter of an outer surface of the first portion; a cover disposed around the outer surface of the first portion, and disposed within the groove; and a second portion having a tab protruding radially inward from an inner surface of the second portion. The tab may be received within the groove, radially outward of the cover.

12 Claims, 8 Drawing Sheets

(51) Int. Cl.
*A61B 1/05* (2006.01)
*A61B 1/06* (2006.01)
*A61B 1/273* (2006.01)

(52) U.S. Cl.
CPC ...... *A61B 1/00098* (2013.01); *A61B 1/00135* (2013.01); *A61B 1/018* (2013.01); *A61B 1/05* (2013.01); *A61B 1/0676* (2013.01); *A61B 1/273* (2013.01)

(56) References Cited

U.S. PATENT DOCUMENTS

| | | | | |
|---|---|---|---|---|
| 5,578,010 | A * | 11/1996 | Ashby | A61M 25/0009 604/523 |
| 5,792,045 | A * | 8/1998 | Adair | A61B 1/00128 600/125 |
| 6,142,945 | A * | 11/2000 | Sakamoto | A61B 8/12 600/459 |
| 2008/0242927 | A1* | 10/2008 | Hirata | G02B 23/2492 600/109 |
| 2012/0209074 | A1* | 8/2012 | Titus | A61B 1/00137 600/153 |
| 2014/0114126 | A1 | 4/2014 | Dresher | |
| 2015/0305733 | A1* | 10/2015 | Albrecht | A61B 17/3431 600/208 |
| 2016/0270637 | A1* | 9/2016 | Tanaka | A61B 1/00098 |
| 2019/0059702 | A1* | 2/2019 | Hosogoe | A61B 1/00101 |
| 2019/0223698 | A1* | 7/2019 | Hosogoe | A61B 1/00098 |
| 2020/0037861 | A1* | 2/2020 | Yamaya | A61B 1/00135 |
| 2020/0214775 | A1* | 7/2020 | Farritor | A61B 1/00057 |

* cited by examiner

COUPLING OF MEDICAL DEVICE COMPONENTS

CROSS-REFERENCE TO RELATED APPLICATIONS

This application claims the benefit of priority of U.S. Provisional Patent Application No. 62/969,837, filed Feb. 4, 2020, the entirety of which is incorporated herein by reference.

TECHNICAL FIELD

The disclosure relates generally to devices, systems, and methods for coupling of medical device components. More specifically, aspects of the disclosure pertain to devices, systems, and/or methods for mechanical coupling of covers to portions of duodenoscopes.

BACKGROUND

Duodenoscopes may include a handle portion, which may be gripped by an operator and may include control elements for functions such as steering, suction, water, air, light, and imaging. A duodenoscope may also include a portion which may be inserted into a subject. For example, a duodenoscope may include a shaft suitable for insertion into a subject. Such an insertion portion may include one or more lumens. The lumens of an insertable portion of a duodenoscope may support functions, for example, conveying air, water, suction, electricity, data, light, and/or images. Tools may also be inserted via a working channel of the shaft. For example, a tool may be inserted by a port in or near the handle of a duodenoscope into the working channel.

A shaft of a duodenoscope may terminate in a steerable distal portion. A distal portion of a duodenoscope may include outlets for air, water, suction, electricity, data, light, images, and/or working tools from lumen(s) of a duodenoscope. A cover may fit over the steerable portion. Fixing the cover to the steerable portion with adhesive can result in imperfections that cause the duodenoscope to fall out of specification and which require scrapping of the duodenoscope. Therefore, a need exists for devices, systems, and methods for coupling of covers to portions of duodenoscopes.

SUMMARY

Examples of the disclosure relate to, among other things, devices, systems, and methods for coupling of components of medical devices, including mechanical coupling of covers to sheaths and/or steerable portions of duodenoscopes. Each of the examples disclosed herein may include one or more of the features described in connection with the disclosed examples.

In one example, a distal end portion of a medical device may comprise: a first portion having a groove around a perimeter of an outer surface of the first portion; a cover disposed around the outer surface of the first portion, and disposed within the groove; and a second portion having a tab protruding radially inward from an inner surface of the second portion. The tab may be received within the groove, radially outward of the cover.

Any of the example devices disclosed herein may include any of the following exemplary features. A constricting element may be positioned within the groove, radially inward of the tab. The constricting element may include at least one of a spring, a string, a wire, a filament, or an O-ring. The cover may include an elastic sleeve. The elastic sleeve and the constricting element may form a single, unitary piece. The groove may includes a straight portion. The tab may be received within the straight portion. The groove may further includes a curved portion. The first portion may include an opening in communication with a working channel of the medical device. The working channel may be configured to receive a medical tool. The distal end portion may further include an imaging device and a lighting source. The imaging device may face a direction that is radially outward from a longitudinal axis of the distal portion. The distal end portion may further include an elevator. The cover may include an elastic sleeve. A first layer of the elastic sleeve may be disposed on a first side of the constricting element. A second layer of the elastic sleeve may be disposed on a second side of the constricting element, opposite the first side. A radial wall of the second portion may include an opening aligned with an imaging device of the first portion. The tab may be received within only a portion of the groove. The tab may extend radially inward from a proximal most edge of the second portion. No adhesive may fix the cover to the groove or the tab. The tab may compress at least a portion of the cover.

An example method of manufacturing a distal end portion of a medical device may comprise positioning a distal end of a cover around an outer surface of a first member and within a groove around a perimeter of the outer surface and positioning a proximal end of a second member radially outward of the first member and the distal end of the cover. The proximal end of the second member may include a tab that is received within the groove, radially outward of the distal end of the core.

Any of the exemplary methods or devices disclosed herein may include any of the following features. The method may further include positioning a constricting element around an outer surface of the cover such that the constricting element is received within the groove. The constricting element may be positioned around an outer surface of a sleeve of the cover. The method may further comprise folding the sleeve of the cover, such that a first layer of the cover is radially inward of the constricting element and a second layer of the cover is radially outward of the constricting element. The constricting element may include at least one of a spring, a string, a wire, a filament, or an O-ring.

Another example method of manufacturing a distal end portion of a medical device may comprise positioning a cover around an outer surface of a first member and within a groove around a perimeter of the outer surface of the first member; and transitioning a portion of the cover from a first configuration to a second configuration. In the second configuration, the portion may have a smaller cross-sectional dimension than in the first configuration. After the portion is transitioned to the second configuration, the portion may be disposed within the groove. The transitioning step may include positioning a proximal end of a second member radially outward of the first member and the portion of the cover. The proximal end of the second member may include a tab that is received within the groove.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "distal" refers to a direction away from an operator/toward a treatment site, and the term "proximal" refers to a direction toward an operator. The term "approximately," or like terms (e.g., "substantially"), includes values +/−10% of a stated value.

BRIEF DESCRIPTION OF THE DRAWINGS

The accompanying drawings, which are incorporated in and constitute a part of this specification, illustrate examples of the present disclosure and together with the description, serve to explain the principles of the disclosure.

FIGS. 3A-4C depict cross-sections of a distal end of a duodenoscope.

DETAILED DESCRIPTION

A duodenoscope may include a sheath or shaft having a steerable distal portion. The steerable distal portion may be coupled to a distal tip. The distal tip may include two components—a cap and a core. A cover may be disposed over the steerable distal portion of the sheath leading to the distal tip. A portion of the cover may be captured between the cap and the core to fix the cover over the steerable distal portion of the sheath. The core may include a groove formed around a perimeter of an outer surface of the core, and the cover may be received within the groove. The cover may include one or more tabs, which may fit within portions of the groove to capture and trap the cover between the tabs and the groove, thereby fixing the cover to the distal tip. The mechanical coupling described herein results in a duodenoscope that meets requirements for tensile strength while improving manufacturing processes and decreasing production costs. In particular, the mechanical coupling allows for production of duodenoscopes meeting manufacturing specifications and minimizing waste resulting from out-of-specification duodenoscopes produced.

Figure 1:
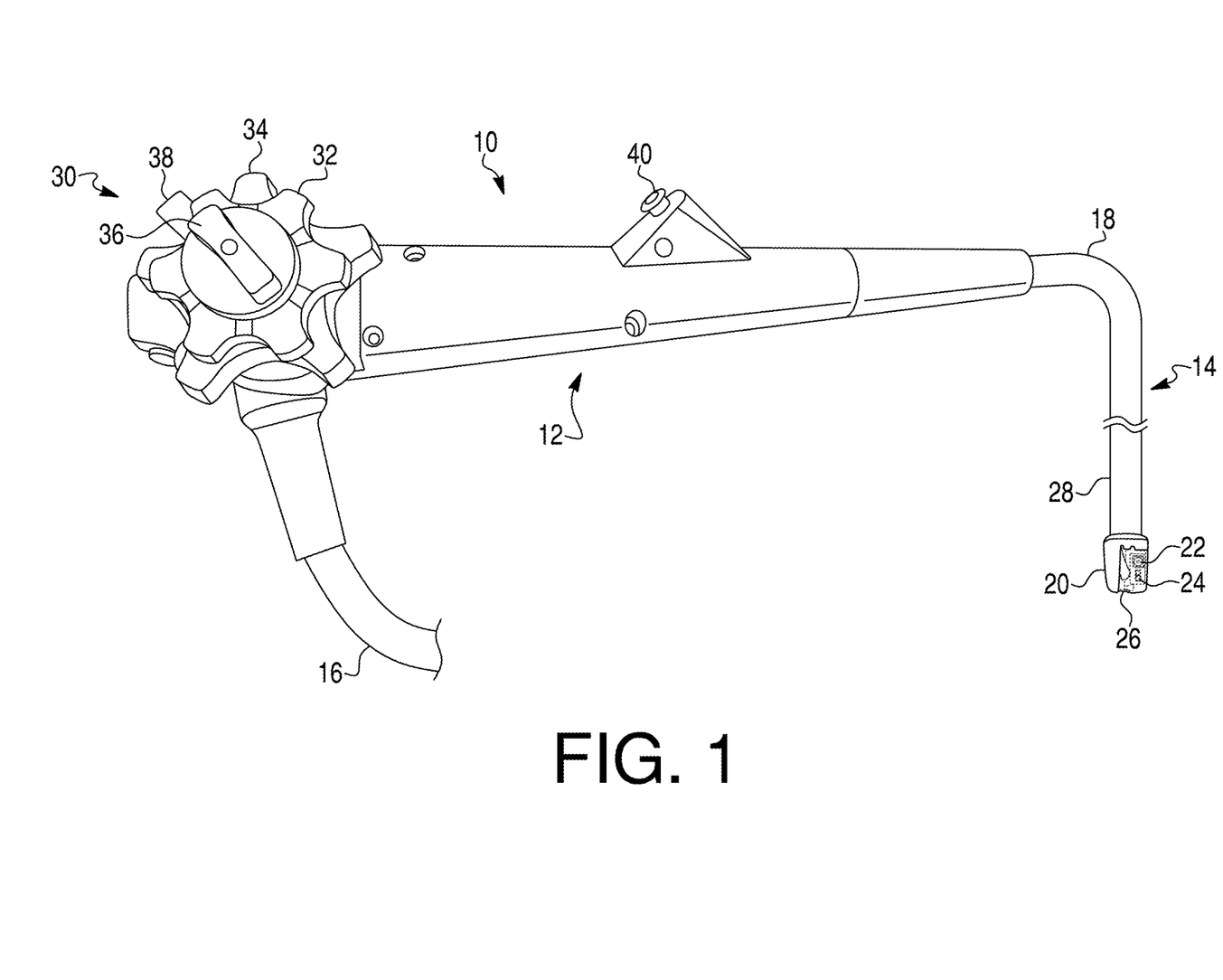
FIG. 1 depicts an exemplary duodenoscope.

FIG. 1 depicts an exemplary duodenoscope 10 having a handle 12 and insertion portion 14. Duodenoscope 10 may also include an umbilicus 16 for purposes of connecting duodenoscope 10 to sources of, for example, air, water, suction, power, etc., as well as to image processing and/or viewing equipment. Although the term duodenoscope may be used herein, it will be appreciated that other devices, including, but not limited to, endoscopes, colonoscopes, ureteroscopes, bronchoscopes, laparoscopes, sheaths, catheters, or any other suitable delivery device or medical device may be used in connection with the coupling devices and methods of this disclosure.

Insertion portion 14 may include a sheath or shaft 18 and a distal tip 20. Distal tip 20 may include an imaging device (e.g., a camera) 22 and a lighting source 24 (e.g., an LED). Distal tip 20 may also include an elevator 26 for changing an orientation of a tool inserted in a working channel of the duodenoscope 10 (further details about insertion of a tool are provided below). Elevator 26 may be pivotable via, e.g., an actuation wire. Distal tip 20 may be side-facing. That is, imaging device 22 and lighting source 24 may face radially outward, perpendicularly or approximately perpendicularly to a longitudinal axis of sheath 18 and distal tip 20.

A distal portion of sheath 18 that is connected to distal tip 20 may have a steerable section 28. Steerable section 28 may be, for example, an articulation joint. Sheath 18 and steerable section 28 may include a variety of structures which are known or may become known in the art. Example features of distal tip 20 are described in further detail with respect to FIGS. 2A-5B, herein.

Handle 12 may have one or more control mechanisms 30. Control mechanisms 30 may provide control over steerable section 28 or may allow for provision of air, water, suction, etc. For example, handle 12 may include control knobs 32, 34 for left, right, up, and/or down control of steerable section 28. For example, one of knobs 32, 34 may provide left/right control of steerable section 28, and the other of knobs 32, 34 may provide up/down control of steerable section 28. Handle 12 may further include one or more locking mechanisms 36 (e.g., knobs or levers) for preventing steering of steerable section 28 in at least one of an up, down, left, or right direction. Handle 12 may include an elevator control lever 38. Elevator control lever 38 may raise and/or lower elevator 26. A port 40 may allow passage of a tool through port 40, into a working channel of the duodenoscope 10, through sheath 18, to distal tip 20.

In use, an operator may insert at least a portion of sheath 18 into a body lumen of a subject. Distal tip 20 may be navigated to a procedure site in the body lumen. The operator may insert a tool (not shown) into port 40, and pass the tool through sheath 18 via a working channel to distal tip 20. The tool may exit the working channel at distal tip 20. The user may use elevator control lever 38 to raise elevator 26 and angle the tool toward a desired location (e.g., a papilla of the pancreatico-biliary tract). The user may use the tool to perform a medical procedure.

Figure 2A:
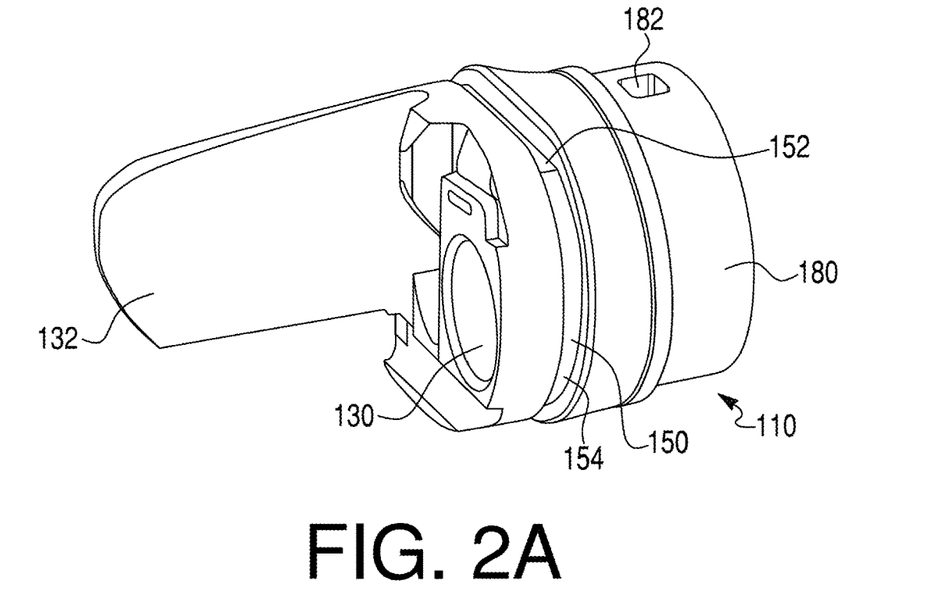
FIGS. 2A and 2B depict exemplary components of a distal end of a duodenoscope.
Figure 2B:
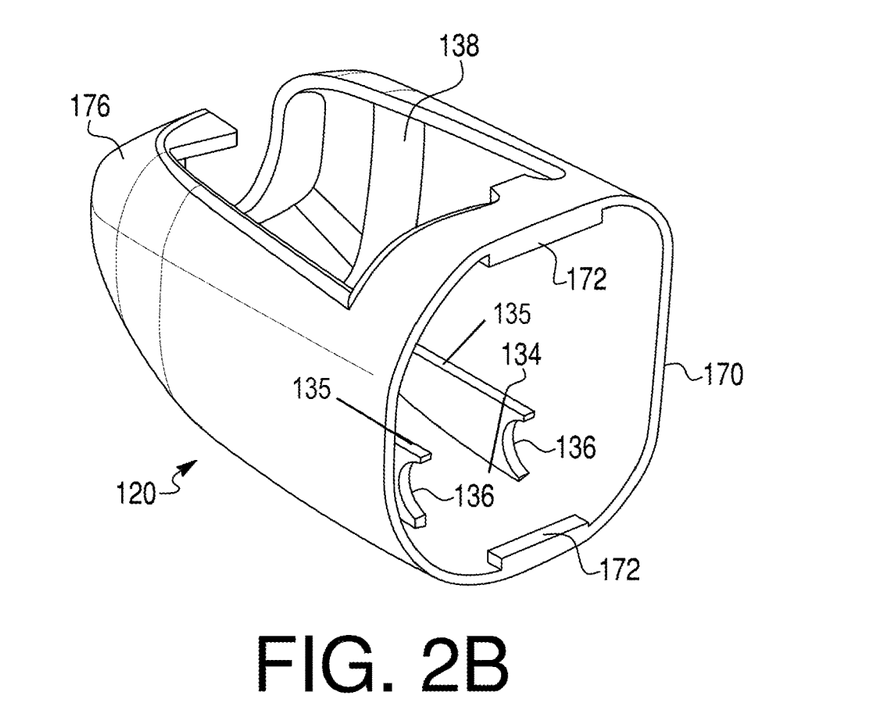

FIG. 2A depicts a distal tip core 110, and FIG. 2B depicts a distal tip cap 120. Together, distal tip core 110 and distal tip cap 120 may form distal tip 20 of duodenoscope 10 or an alternative distal tip of an alternative device. Core 110 may receive components, such as imaging device 22 and lighting source 24. For example, a module having imaging device 22 and lighting source 24 may be fixed to a fin 132 of core 110 that extends parallel to or approximately parallel to a longitudinal axis of distal tip 20/sheath 18. Core 110 may also include outlets for air, water, and/or suction. Core 110 may include an opening 130 in communication with a working channel of duodenoscope 10. Tools passed though the working channel may exit opening 130 in order to perform procedures in a body lumen of a patient.

Cap 120 may fit over at least a portion of core 110 (as shown in FIGS. 3A-5B). A surface of fin 132 that is opposite imaging device 22 and lighting source 24 may mate with an inner surface of cap 120. Cap 120 may include elevator housing 134 bounded by two walls 135. Housing 134 may receive elevator 26 and allow rotation of elevator 26 therein. To facilitate rotation of elevator 26, walls 135 may include recessed portions 136 for receiving a hinge of elevator 26. Cap 120 may include an opening 138. When core 110 is received within cap 120 (see FIGS. 3A-5B), opening 138 may align with imaging device 22 and/or lighting source 24 to allow imaging device 22 and/or lighting source 24 to allow transmission of images and/or light. Opening 138 may also align with elevator 26 to allow maneuvering of tools passed through the working channel.

Core 110 may include a groove 150 around a perimeter of core 110, on an outer surface of core 110, proximal of opening 130. Groove 150 may include two straight (or substantially straight) portions 152, on opposite sides of core 110. One of straight portions 152 may be on a same side of distal tip 20 as imaging device 22 and/or lighting source 24. Straight portions 152 may be parallel or approximately parallel to one another. Straight portions 152 may extend perpendicularly or approximately perpendicularly to a longitudinal axis of distal tip 20. Groove 150 may include two curved portions 154, extending between straight portions 152. Curved portions 154 may have a shape that is similar or approximately similar to that of an outer surface of cap 120. Alternative numbers of straight portions 152 and/or curved portions 154 may be used.

Cap 120 may have a proximal surface 170 that may align with groove 150 when cap 120 is disposed on core 110. Tabs 172 may be formed on proximal surface 170, extending radially inward from proximal surface 170 and/or radially inward from an inner surface of cap 120. As shown in FIG. 2B, cap 120 may include two tabs 172. Alternatively, other numbers of tabs 172 may be used. A number of tabs 172 may be equal to a number of straight portions 152. One of tabs 172 may be on a same side of distal tip 20 as opening 138 of cap 120, and the other tab 172 on an opposing side. As described in further detail below, tabs 172 may be received within straight portions 152 of groove 150. Cap 120 may extend from proximal surface 170 to a distal end 176.

Core 110 may also include a mating surface 180 for mating with a distal end of steerable section 28. For example, mating surface 180 may be received within a lumen of steerable section 28 and may mate with an inner surface of steerable section 28. Core 110 may include recesses 182, which may be mated with tabs or protrusions of a distal end of steerable section 28 (see FIGS. 5A-5B).

FIGS. 3A-5B show devices in which a cover 210 has been trapped between cap 120 and core 110. Cover 210 may extend proximally from a joint 202 (see FIGS. 5A and 5B) between cap 120 and core 110. As discussed in further detail below, a constricting member or element 212 may facilitate effectively securing cover 210 between cap 120 and core 110. In particular, constricting member 212, as well as other aspects of distal tip 20, described below, may enable cover 210 to withstand the forces (e.g., tensile forces) on the cover 210 due to insertion of sheath 118 into a body lumen, navigation of sheath 118 within the body lumen, and/or steering of steerable section 28.

Figure 3A:
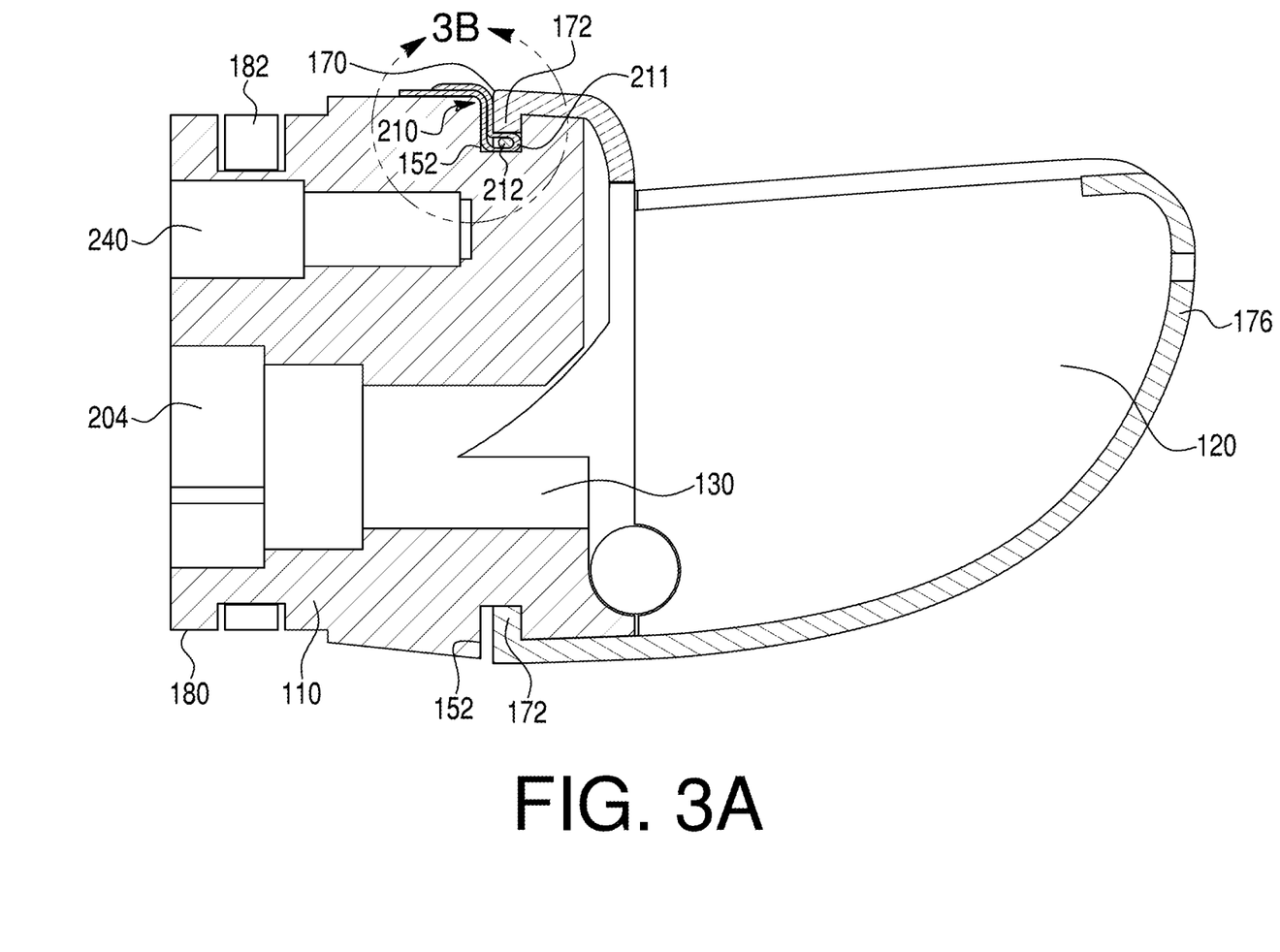
Figure 3B:
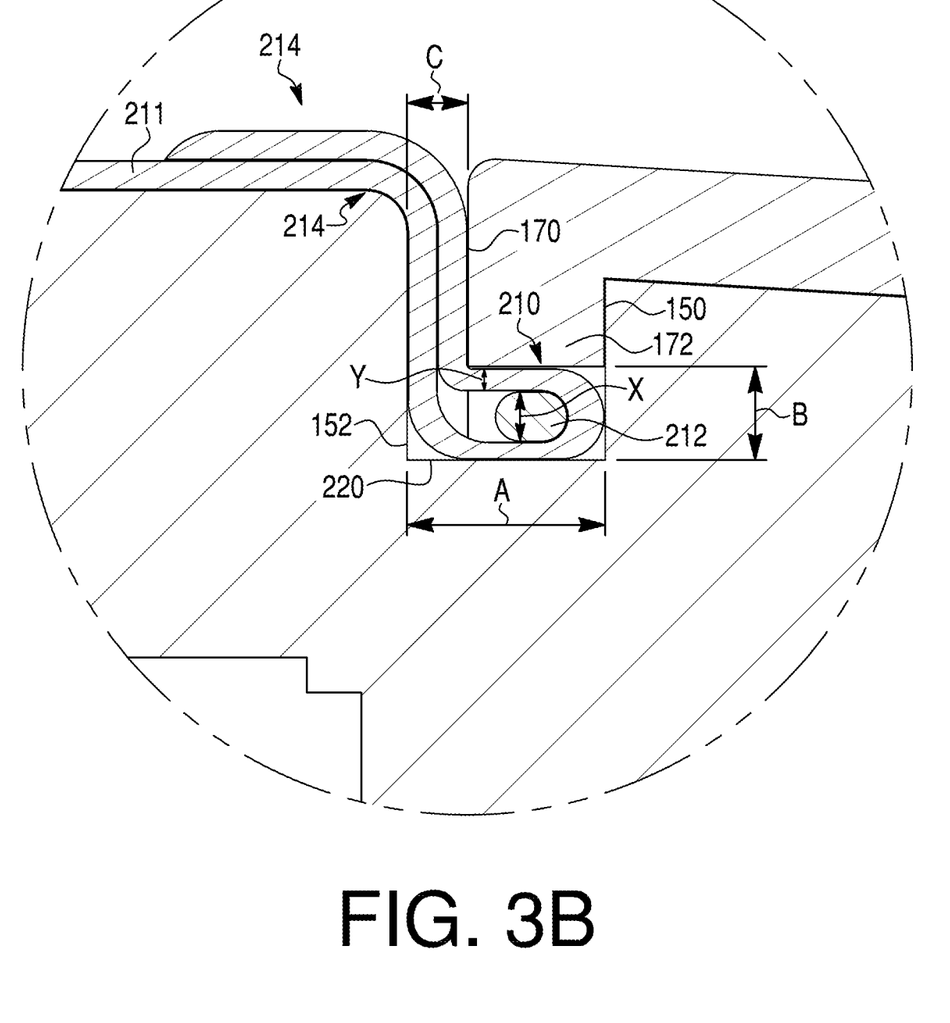
Figure 4A:
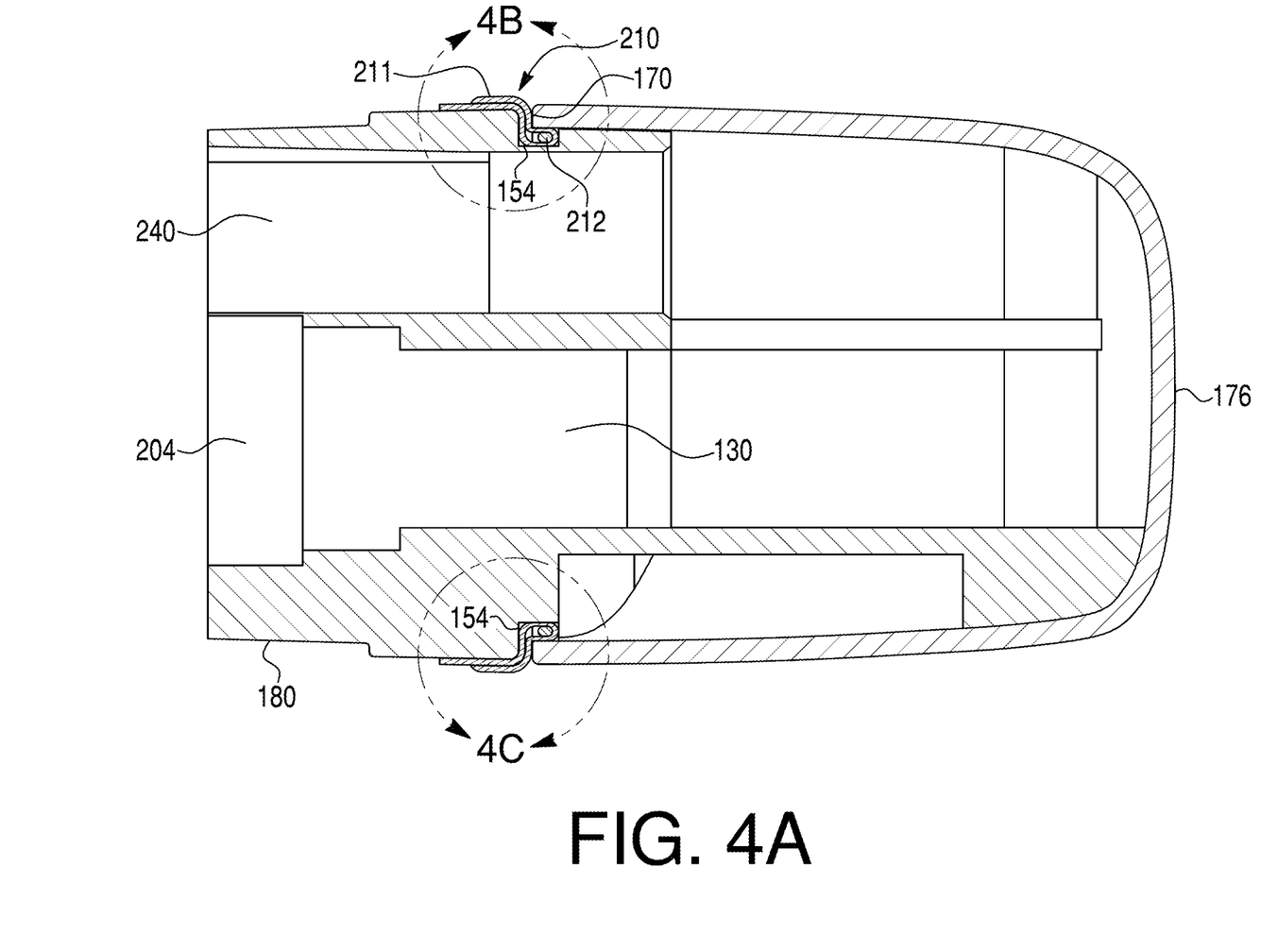
Figure 4B:
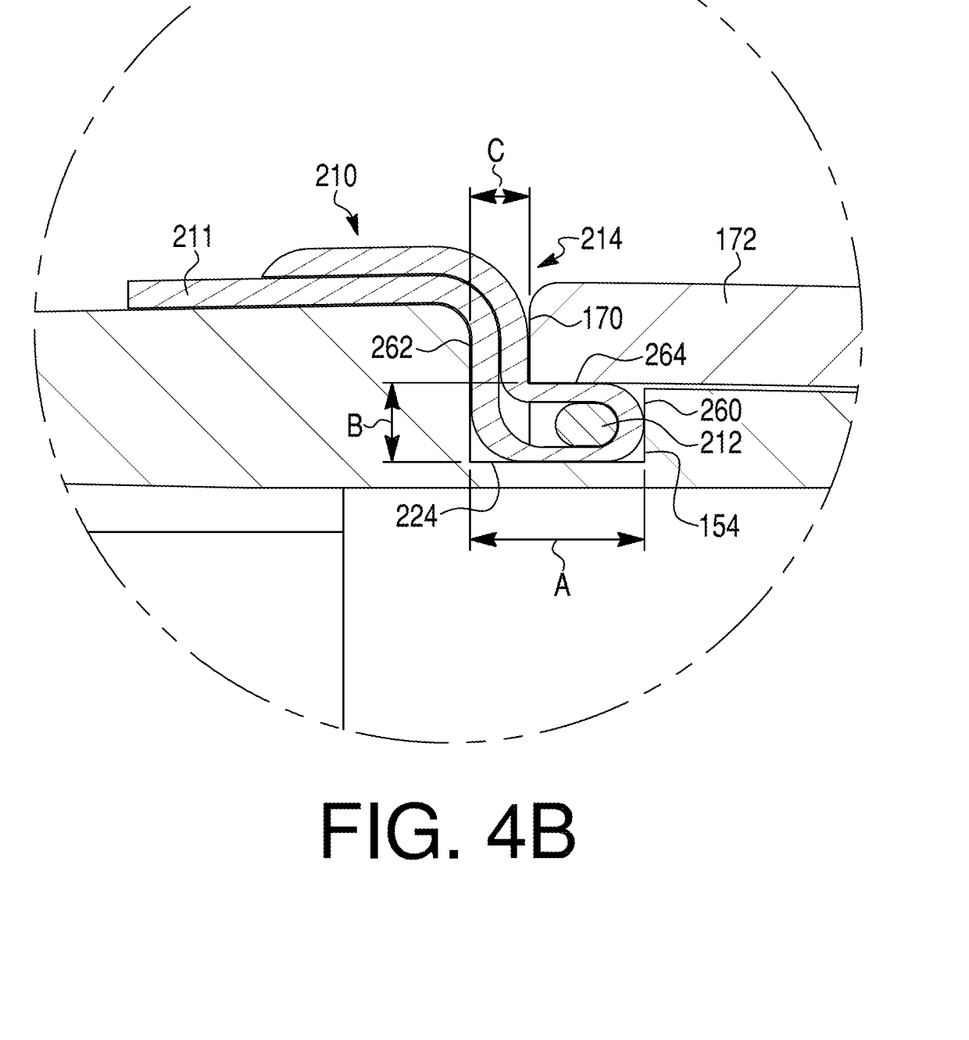
Figure 4C:
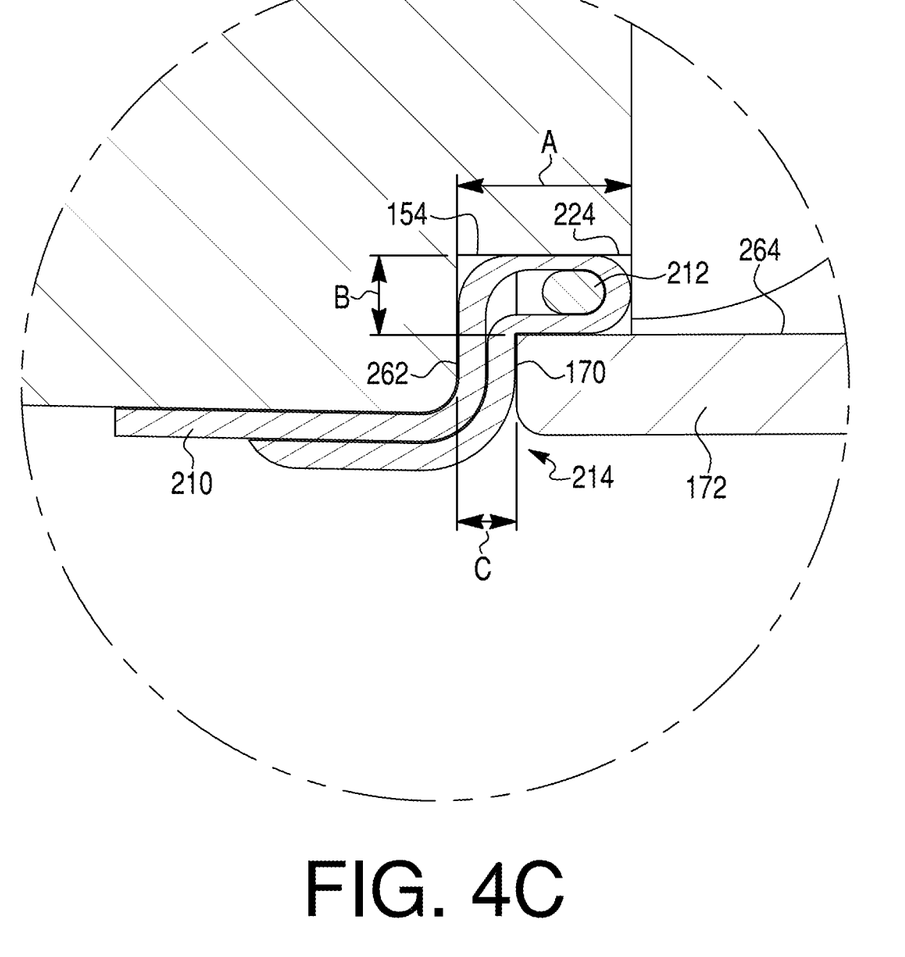

FIG. 3A shows a cross-sectional view of distal tip 20, taken along a longitudinal axis of distal tip 20, through tabs 172 and straight portions 152. FIG. 3B shows an enlarged view of the circled portion 3B of FIG. 3A. Although, for the ease of illustration, FIG. 3A only shows cover 210 as being on one side of distal tip 20 (corresponding to the enlarged portion shown in FIG. 3B), it will be appreciated that cover 210 may extend around an entire perimeter of distal tip 20. FIG. 4A shows a cross-sectional view of distal tip 20, taken along a longitudinal axis of distal tip 20, through curved portions 154. FIGS. 4B and 4C show enlarged views of circled portions 4B and 4C, respectively.

As shown in FIGS. 3A and 4A, a proximal end of core 110 of distal tip 20 may include a mating portion 204 for mating with a working channel (not shown) of duodenoscope 10. Mating portion 204 may be in fluid communication with opening 130. Distal tip 20 may also include a channel or cavity 240 for receiving wiring, tubing, or other components that pertain to delivering, e.g., air or water or transmitting signals or power to/from imaging device 22 and/or lighting source 24.

In FIGS. 3A-4C, cap 120 has been fitted over core 110. Additionally, cover 210 has been fitted over a portion of core 110 including and proximal to groove 150. Cover 210 may extend proximally to cover steerable section 28 (not shown in the Figures). Cover 210 may include a sleeve 211 (which may be flexible and/or elastic) and constricting member 212, at a distal end of cover 210. Sleeve 211 may include, for example, an elastic fabric, polymer, plastic, mesh, braid, woven material, knit material, molded material, and/or other suitable material. Constricting member 212 may be disposed within groove 150, along with portion(s) or layer(s) of sleeve 211. Constricting member 212 may be disposed radially outward of at least one layer of sleeve 211. Constricting member 212 may have properties such that constricting member 212 retains sleeve 211 within groove 150.

Constricting member 212 may include, for example, an O-ring (e.g., nitrile O-ring), a string, a filament (e.g., a nylon filament), a spring, fluorinated ethylene propylene heat shrink, Nitinol (e.g., a heat-shrink nitinol ring), a zip tie, or other structure or material. Constricting member 212 may be disposed about an outer surface of at least a layer of sleeve 211 near a distal end of sleeve 211. Constricting member 212 may be secured or attached to sleeve 211 via adhesive, stitching, or other mechanisms. Alternatively, constricting member 212 may be disposed about flexible sleeve without adhesive or other mechanisms.

Alternatively, constricting member 212 may be formed integrally with sleeve 211. Constricting member 212 may form a single, unitary piece with sleeve 211. For example, sleeve 211 may be molded, and constricting member 212 may be formed by the molding process. For example, constricting member 212 may have a lip-like or ring-like shape, and may have a smaller outer diameter when in a relaxed state than a remainder of cover 210. Constricting member 212 may be elastic and capable of being enlarged to fit over core 110, similar to an O-ring. Where constricting member 212 is an integral portion of sleeve 211, constricting member 212 may be made of the same material as sleeve 211 (e.g., be a thickened portion of sleeve 211) or may be a different material than sleeve 211. In another alternative, a constricting member 212 made from a material such as those described above (e.g., wire, O-ring, or filament) may have flexible sleeve 211 overmolded thereon, so that sleeve 211 and constricting member 212 form one piece. In another example, a constricting member 212 (e.g., a filament or a string) may be slidably woven through sleeve 211 such that constricting member 212 acts like a drawstring around sleeve 211.

Figure 5A:
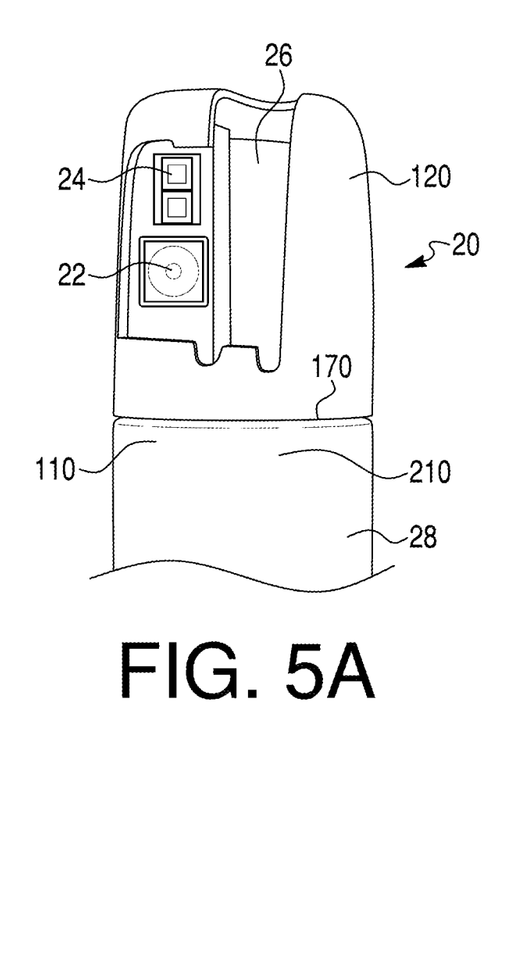
FIGS. 5A-5B depict exemplary distal ends of a duodenoscope.
Figure 5B:
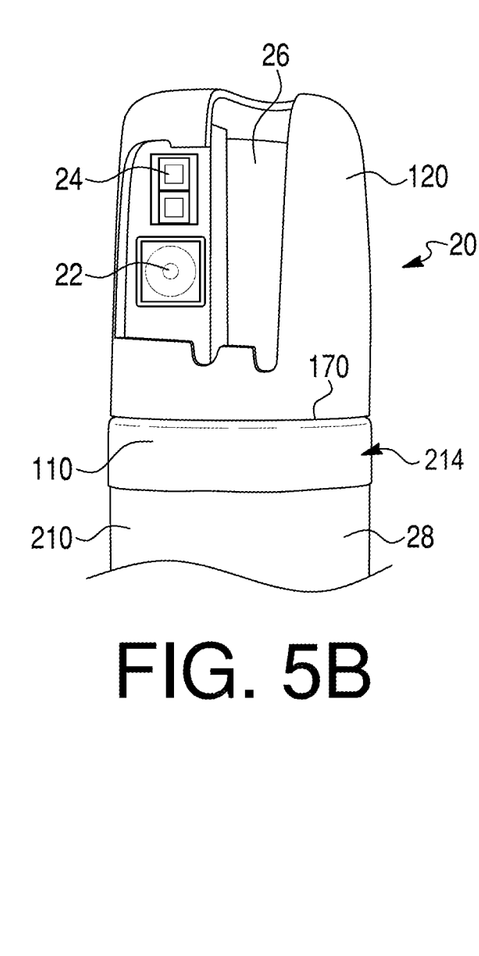

In order to fix cover 210 between core 110 and cap 120, sleeve 211 may be slid or otherwise placed around an outer surface of core 110. Sleeve 211 may be positioned so that a desired portion is radially around (outside of) core 110, around groove 150. Sleeve 211 may be positioned so that a distal end of sleeve 211 extends distally past groove 150. In such a case, flexible sleeve 211 may be folded proximally after constricting member 212 is positioned, as discussed below and as shown in FIG. 5B. Alternatively, sleeve 211 may be positioned so that a distal end of sleeve 211 aligns with or approximately aligns with groove 150. In such a case, flexible sleeve 211 may not be folded proximally after constricting member 212 is positioned, as shown in FIG. 5A.

After sleeve 211 is positioned, constricting member 212 may be positioned around (radially outward of) sleeve 211 at the position of groove 150. If sleeve 211 and constricting member 212 are one integral element or otherwise joined, sleeve 211 and constricting member 212 may be placed together around an exterior surface of core 110 such that constricting member 212 is about groove 150.

Constricting member 212 may tighten around sleeve 211, exerting a force on sleeve 211 to push it within groove 150 and retain it within groove 150. Constricting member 212 may transition from a first configuration, in which constricting member 212 has a first cross-sectional dimension (e.g., width, which may be a diameter) to a second configuration, in which constricting member 212 has a second cross-sectional width, smaller than the first cross-sectional width. The transition of constricting member 212 may cause constricting member 212, and sleeve 211, to be retained within groove 150.

For example, constricting member 212 may be an elastic member (e.g., an O-ring) that may be stretched to be placed about sleeve 211 and core 110. Alternatively, where an O-ring type constricting member 212 is formed integrally with sleeve 211, sleeve 211 and constricting member 212 may be placed together around core 110, while constricting member 212 is stretched. When constricting member 212 is released, a cross-sectional diameter of constricting member 212 may decrease as material properties of constricting member 212 urge constricting member 212 toward its natural cross-sectional diameter. The elastic constricting member 212 may thus tighten about sleeve 211, within groove 150. Alternatively, constricting member 212 may be tied, ratcheted (like, e.g., a zip tie), or otherwise tightened about sleeve 211, within groove 150, to transition constricting member 212 from the first configuration to the second configuration. For example, where constricting member 212 is a filament or a string, the filament or string may be placed about sleeve 211 and tightened. Where constricting member 212 includes a wire or a spring (e.g., a Nitinol wire or spring), the wire can be wrapped around sleeve 211, within groove 150. A wire or string may be wrapped multiple times (e.g., twice, three times, etc.). Where constricting member 212 includes heat-shrink material (e.g., FEP heat shrink), constricting member 212 may be positioned about groove 150, and heat may be applied to tighten/constrict constricting member 212 within groove 150.

If desired, a portion of flexible sleeve 211 may be folded proximally over constricting member 212 to form a folded portion 214, as shown in FIGS. 3A-4C and 5B. If sleeve 211 is folded, sleeve 211 may envelop constricting member 212 (surrounds constricting member 212 on inner and outer sides), with constricting member 212 at a distal end of folded sleeve 211. A first layer of sleeve 211 may be on one side of constricting member 212, and a second layer of flexible sleeve 211 may be on another, opposite side of constricting member 212. Alternatively, sleeve 211 may not be folded, and constricting member 212 may be outside of sleeve 211 on a distal end of sleeve 211 (or formed integrally with sleeve 211, as described above).

After constricting member 212 is positioned about sleeve 211, such that constricting member 212 is positioned within groove 150, cap 120 may be positioned such that a distal end of core 110 faces a proximal opening of cap 120. Cap 120 may be moved proximally relative to core 110, until tabs 172 engage with and are disposed within straight portions 152 of groove 150, as shown in FIGS. 3A-3B. Tabs 172 may snap fit with groove 150, creating an interference fit due to the dimensions of groove 150, tabs 172, and cover 210, described in further detail below. Alternatively, other methods of attaching cap 120 to core 110 may be used (e.g., screw fit, friction fit, etc.) Tabs 172 may further secure constricting member 212 and sleeve 211 within groove 150 and may fix cap 120 to core 110 to form distal tip 20. Without the presence of constricting member 212, cap 120 may displace sleeve 211 without trapping and securing sleeve 211 within groove 150.

Tabs 172 may be radially outward of cover 210 (sleeve 211 and constricting member 212). An outer surface of cap 120 at proximal surface 170 may be approximately level (in a radial direction) with an outer surface of cover 210 (or an outer surface of a radially inner layer of sleeve 211, as shown in the Figures) proximal to groove 150. Cap 120 may include a ledge (not shown) that extends proximally over the portion of cover 210 trapped between cap 120 and core 110. Before or after cap 120 is positioned over core 110, cover 210 (including, e.g., sleeve 211) may be reflowed to increase strength of attachment of cover 210 and a seal of cover 210 over distal tip 20.

As shown in FIGS. 4A-4B, tabs 172 may not extend into curved portions 154 of groove 150. Instead, proximal surface 170 may be radially outward of an inner wall 224 of curved portion 154, as well as cover 210 (including sleeve 211 and constricting member 212). A distal wall 260 of curved portion 154 may be shorter than a proximal wall 262 of curved portion 154. As shown in FIG. 4C, distal wall 260 may not extend entirely around groove 150/curved portion 154, and may be absent in portions. An inner surface 264 of cap 120 may be more radially inward than a radially outward end of proximal wall 262. An outer surface of cap 120 at proximal surface 170 may be approximately level (in a radial direction) with an outer surface of cover 210 (or an outer surface of a radially inner layer of sleeve 211, as shown in the Figures) proximal to groove 150.

Straight portions 152, sleeve 211, and constricting member 212 may be dimensioned such that, when tabs 172 are received within straight portions 152, sleeve 211 is secured about distal tip 20. For example, a depth B (see FIG. 3B) of a portion of straight portion 152 not occupied by tab 172 (a distance between a radially inner surface of tab 172 and a radially inner wall 220 of straight portion 152 may be smaller than a cross-sectional width X of uncompressed constricting member 212 (along a radial direction of distal tip 20, parallel to depth B) plus an uncompressed total thickness of the one or more layer(s) of sleeve 211 (each of which may have an uncompressed thickness Y). Cross-sectional width X is shown in the Figure for reference as to the direction of cross-sectional width X, although constricting member 212 is compressed in FIG. 3B. Tab 172 may compress constricting member 212 and/or sleeve 211. This compression holds cover 210 (constricting member 212 and sleeve 211) in place against an inner wall 220 of straight portion 152. As shown in FIG. 3B, compressed constricting member 212 may have a non-circular cross section because constricting member 212 has been compressed by tab 172. Inner wall 220 of groove 150 may have a width A, along a longitudinal axis of distal tip 20. A portion of width A not occupied by tab 172 may have a dimension C that is smaller than a total thickness Y of the one or more uncompressed layer(s) of sleeve 211 positioned therein. Tab 172 may compress sleeve 211 in the portion of width A not occupied by tab 172, further securing cover 210.

Dimensions of curved portion 154 may be similar to those of straight portion 152. In particular, the space to be occupied by cover 210 may be the same or approximately the same in curved portion 154 and straight portion 152. With respect to curved portion 154, dimension B may represent a distance between inner surface 264 and inner wall 224. For example, width A, depth B, and dimension C of curved portion 154 may be equal to width A, depth B, and dimension C, respectively, of straight portion 152. Therefore, cover 210 may also be compressed within curved portion 154, by surfaces 264 and 170.

By way of non-limiting example, depth B may be approximately 0.017 inches. Width A may be approximately 0.037 inches. Dimension C may be approximately 0.011 inches. Sleeve 211 may have an uncompressed thickness of approximately 0.010 inches. Constricting member 212 may have an uncompressed cross-sectional thickness of approximately 0.010 inches. Because dimension B is smaller than a total thickness of cover 210 (sleeve 211 and constricting member 212), tab 172 may exert a radially inward force on cover 210, compressing sleeve 211 and/or constricting member 212. Similarly, because width C is smaller than a thickness of cover 210 (e.g., the one or more layers of sleeve 211), proximal surface 170 of cap 120 may exert a proximal, compressing force on cover 210. These compressive forces may serve to secure cover 210, providing sealing between cover 210 and distal tip 20, and preventing cover 210 from becoming disconnected from distal tip 20 when subjected to forces, including the tensile forces descried above. Similarly, surfaces 264 and 170 may compress cover 210 within curved portion(s) 154 of groove 150.

FIGS. 5A and 5B depict perspective views of an assembled distal tip 20. FIG. 5A depicts an example in which sleeve 211 of cover 210 is not folded to form a folded portion. FIG. 5B depicts an example in which sleeve 211 is folded back to form a folded portion 214. As shown in FIGS. 5A and 5B, the devices and methods described herein may result in a distal tip 20 joined to a steerable section 28, without using adhesive on sleeve 211 or distal tip 20 (including, e.g., on groove 150). Cover 210 may extend proximally from joint 202 between core 110 and cap 120.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A distal end portion of a medical device, the distal end portion comprising:
a first portion having a groove around a perimeter of an outer surface of the first portion;
a cover disposed around the outer surface of the first portion, and disposed within the groove, wherein the cover includes an elastic sleeve, and wherein the elastic sleeve includes a folded portion;
a second portion having a tab protruding radially inward from an inner surface of the second portion, wherein the tab is received within the groove, radially outward of the cover; and
a constricting element positioned within the groove, radially inward of the tab, wherein the folded portion of the elastic sleeve surrounds the constricting element.

2. The distal end portion of claim 1, wherein the constricting element includes at least one of a spring, a string, a wire, a filament, or an O-ring.

3. The distal end portion of claim 1, wherein the groove includes a straight portion, and wherein the tab is received within the straight portion.

4. The distal end portion of claim 3, wherein the groove further includes a curved portion.

5. The distal end portion of claim 1, wherein the first portion includes an opening in communication with a working channel of the medical device, wherein the working channel is configured to receive a medical tool.

6. The distal end portion of claim 1, further comprising an imaging device and a lighting source, wherein the imaging device faces a direction that is radially outward from a longitudinal axis of the distal end portion.

7. The distal end portion of claim 1, further comprising an elevator.

8. The distal end portion of claim 1, wherein the tab is received within only a portion of the groove.

9. The distal end portion of claim 1, wherein the tab compresses at least a portion of the cover.

10. A distal end portion of a medical device, the distal end portion comprising:
a first portion having a groove around a perimeter of an outer surface of the first portion;
a cover disposed around the outer surface of the first portion, and disposed within the groove, wherein the cover has a distalmost end, wherein the cover includes a folded portion;
a second portion having a body received within the groove, radially outward of the cover; and
a constricting element positioned within the groove of the first portion, wherein the constricting element is radially inward of the body, and wherein the folded portion of the cover surrounds the constricting element.

11. The distal end portion of claim 1, wherein the first portion is a core portion, and wherein the second portion is a cap portion, and wherein the core portion is proximal of the cap portion.

12. The distal end portion of claim 11, wherein the cap portion is configured to receive at least a portion of the core portion.

* * * * *